US012577178B2

(12) United States Patent
Murakami et al.

(10) Patent No.: US 12,577,178 B2
(45) Date of Patent: *Mar. 17, 2026

(54) SLIDING MEMBER AND METHOD OF MANUFACTURING SLIDING MEMBER

(71) Applicant: KYOCERA CORPORATION, Kyoto (JP)

(72) Inventors: Takayuki Murakami, Oumiyahata (JP); Taito Nakamura, Yasu (JP); Junji Ikeda, Osaka (JP)

(73) Assignee: KYOCERA Corporation, Kyoto (JP)

( * ) Notice: Subject to any disclaimer, the term of this patent is extended or adjusted under 35 U.S.C. 154(b) by 490 days.

This patent is subject to a terminal disclaimer.

(21) Appl. No.: 18/010,203

(22) PCT Filed: Jun. 1, 2021

(86) PCT No.: PCT/JP2021/020799
§ 371 (c)(1),
(2) Date: Dec. 13, 2022

(87) PCT Pub. No.: WO2022/004242
PCT Pub. Date: Jan. 6, 2022

(65) Prior Publication Data
US 2023/0233330 A1 Jul. 27, 2023

(30) Foreign Application Priority Data
Jul. 2, 2020 (JP) ................................. 2020-114933

(51) Int. Cl.
*C04B 41/53* (2006.01)
*C04B 41/91* (2006.01)
(Continued)

(52) U.S. Cl.
CPC .......... *C04B 41/5353* (2013.01); *C04B 41/91* (2013.01); *C09K 13/04* (2013.01);
(Continued)

(58) Field of Classification Search
CPC ..... C04B 41/5353; C04B 41/91; C04B 35/10; C04B 2235/3217; C04B 2235/3244;
(Continued)

(56) References Cited

U.S. PATENT DOCUMENTS 6,553,788 B1 * 4/2003 Ikeda ...................... C03C 15/00
216/97
2002/0198602 A1 * 12/2002 Nawa .................... A61L 27/427
623/23.56
(Continued)

FOREIGN PATENT DOCUMENTS

ES 2594032 A1 * 12/2016 ............. C04B 41/91
JP 06297254 A * 10/1994 ......... C04B 41/0027
(Continued)

OTHER PUBLICATIONS

JP 2828565 "Ceramic Sliding Member an Method of Manufacturing the Same" English machine translation (Year: 1998).*
(Continued)

*Primary Examiner* — Anita K Alanko
(74) *Attorney, Agent, or Firm* — Procopio, Cory, Hargreaves & Savitch LLP

(57) ABSTRACT

To provide a sliding member having improved wear resistance, and a method of manufacturing the sliding member. A femoral head ball according to an aspect of the present disclosure includes a composite ceramic containing alumina and at least one oxide other than alumina. A surface roughness Ra of the sliding surface when the femoral head ball slides against a constituent member constituting an artificial joint is not more than 0.01 μm. The sliding surface includes a plurality of recessed portions each having an opening diameter of not more than 2 μm.

9 Claims, 7 Drawing Sheets

(51) Int. Cl.

| | |
|---|---|
| *C09K 13/04* | (2006.01) |
| *A61F 2/30* | (2006.01) |
| *A61F 2/36* | (2006.01) |
| *A61L 27/10* | (2006.01) |
| *A61L 27/18* | (2006.01) |
| *C04B 35/10* | (2006.01) |

(52) U.S. Cl.
CPC ........... *A61F 2/3094* (2013.01); *A61F 2/3609* (2013.01); *A61F 2002/3611* (2013.01); *A61F 2310/00203* (2013.01); *A61F 2310/00239* (2013.01); *A61L 27/105* (2013.01); *A61L 27/18* (2013.01); *A61L 2430/02* (2013.01); *C04B 35/10* (2013.01); *C04B 2235/3217* (2013.01); *C04B 2235/3244* (2013.01); *C04B 2235/786* (2013.01); *C04B 2235/963* (2013.01)

(58) Field of Classification Search
CPC ......... C04B 2235/786; C04B 2235/963; A61F 2/3094; A61F 2/3609; A61F 2/34; A61F 2/36; A61F 2002/3611; A61F 2310/00203; A61F 2310/00239; A61L 27/105; A61L 27/18; A61L 2430/02; C09K 13/04
See application file for complete search history.

(56) References Cited

U.S. PATENT DOCUMENTS

| | | | | |
|---|---|---|---|---|
| 2003/0031878 A1* | 2/2003 | Mitani | ................... | C03C 15/00 |
| | | | | 428/846.9 |
| 2004/0267376 A1* | 12/2004 | Suzuki | ................... | A61L 27/30 |
| | | | | 623/23.5 |
| 2005/0049716 A1* | 3/2005 | Wagener | ................ | A61L 27/50 |
| | | | | 623/23.51 |
| 2007/0225823 A1* | 9/2007 | Hawkins | ................ | A61L 27/28 |
| | | | | 428/420 |
| 2008/0071381 A1* | 3/2008 | Buscher | ................... | A61F 2/32 |
| | | | | 623/18.11 |
| 2008/0275568 A1 | 11/2008 | Shikata | | |
| 2010/0016989 A1* | 1/2010 | Lyngstadaas | ........... | A61L 27/56 |
| | | | | 623/23.72 |
| 2012/0221110 A1 | 8/2012 | Nakanishi | | |

FOREIGN PATENT DOCUMENTS

| | | | | | |
|---|---|---|---|---|---|
| JP | 08-004770 A | | 1/1996 | | |
| JP | 09-110517 A | | 4/1997 | | |
| JP | 2828565 B2 | * | 11/1998 | .......... | C04B 41/009 |
| JP | 2005034630 A | | 2/2005 | | |
| JP | 2010-248051 A | | 11/2010 | | |
| JP | 4646554 B2 | * | 3/2011 | | |
| WO | 2002011780 A1 | | 2/2002 | | |
| WO | 2005042047 A1 | | 5/2005 | | |
| WO | 2011049176 A1 | | 4/2011 | | |

OTHER PUBLICATIONS

JP 06297254 A English abstract (Year: 1994).*
ES 2594032 A1, English-language translation, "Method for selective pickling of zirconia located on the surface of a ceramic material comprising an Al2O3 matrix" (Year: 2016).*
JP 4646554 B2, English-language translation, "Ceramic member for living body implant and manufacturing method thereof" (Year: 2011).*

* cited by examiner

SLIDING MEMBER AND METHOD OF MANUFACTURING SLIDING MEMBER

TECHNICAL FIELD

The present disclosure relates to a sliding member and a method of manufacturing the sliding member.

BACKGROUND OF INVENTION

A known artificial joint includes a pair of joint members that constitute the joint. Between the pair of joint members, a pair of friction surfaces that slide relative to each other while in contact with each other via lubricating fluid are formed. In one known artificial joint, at least one of the pair of friction surfaces includes a recessed portion and a curved surface portion. The recessed portion has at least a groove shape or hole shape that becomes progressively narrower inward from the surface of the friction surface. The curved surface portion seamlessly connects the surface forming the recessed portion and the surface forming the surface portion of the friction surface.

Generally, as the surface roughness Ra of the friction surface increases, the cutting wear amount increases. On the other hand, as the surface roughness Ra of the friction surface decreases, the adhesive wear amount increases. Therefore, there is a surface roughness Ra at which the sum of the cutting wear amount and the adhesive wear amount is the smallest and wear resistance is improved.

In an aspect of the present disclosure, a sliding member includes a sliding surface configured to slide against a constituent member constituting an artificial joint, and a composite ceramic containing alumina and at least one oxide other than alumina. The sliding surface includes a plurality of recessed portions each having an opening diameter of not more than 2 μm, and a surface roughness Ra of the sliding surface is not more than 0.01 μm.

In an aspect of the present disclosure, a method of manufacturing a sliding member includes polishing a surface of a composite ceramic containing alumina and at least one oxide other than alumina, and acid-treating the polished surface with a strong acid solution to form a recessed portion in the surface.

DESCRIPTION OF EMBODIMENTS

First Embodiment

Configuration of Artificial Hip Joint 1

Figure 1:
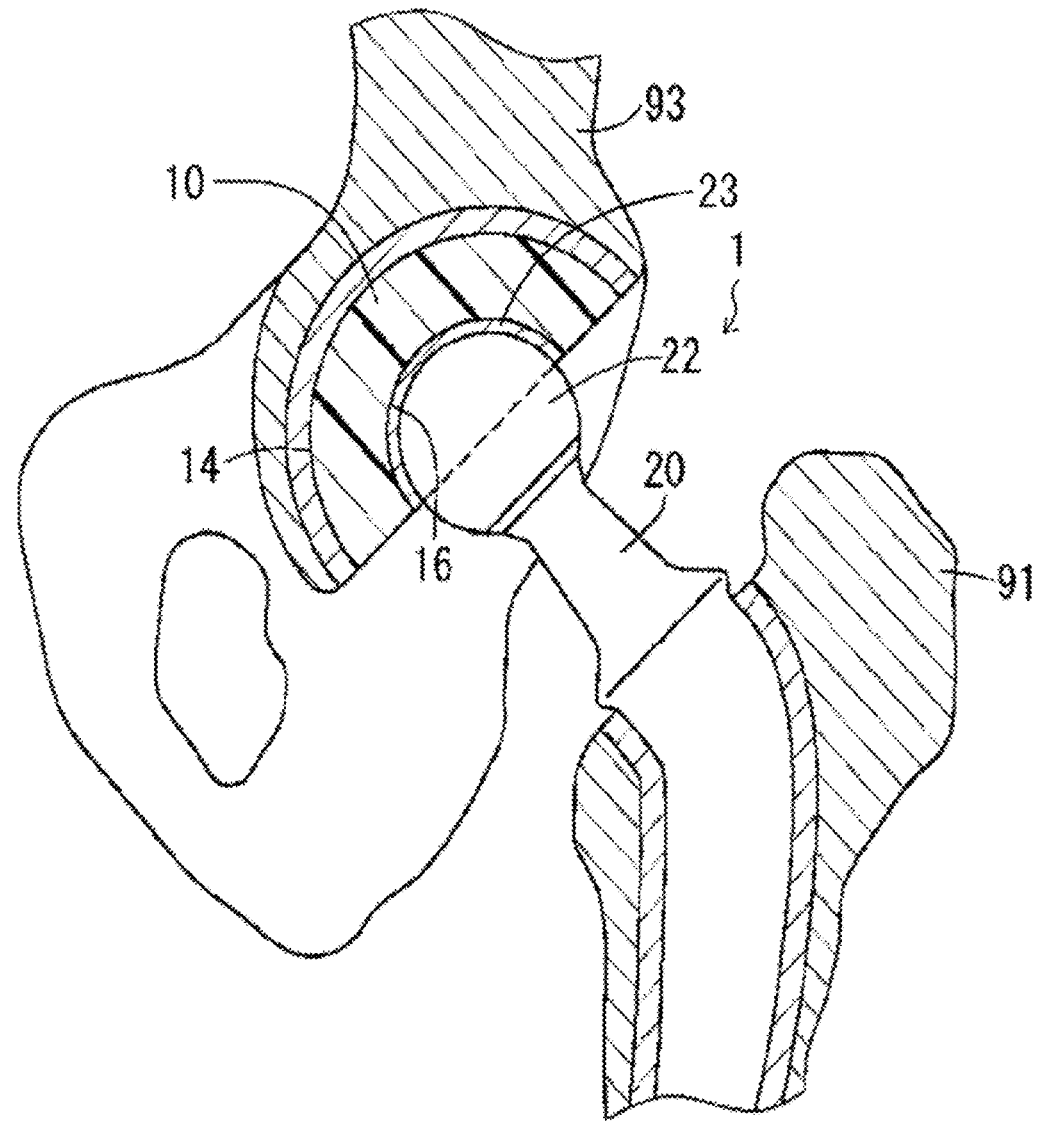
FIG. 1 is a schematic view of an artificial hip joint according to an embodiment of the present disclosure.

An embodiment of the present disclosure will be described in detail below. FIG. 1 is a schematic view of an artificial hip joint 1 serving as an artificial joint according to an embodiment of the present disclosure. As illustrated in FIG. 1, the artificial hip joint 1 is constituted by an acetabular cup 10 to be fixed to an acetabulum of a hip bone 93, a femoral stem 20 to be fixed to a proximal end of a femur 91, and a femoral head ball 22 that slides with the acetabular cup 10. That is, the acetabular cup 10, the femoral stem 20, and the femoral head ball 22 are constituent members that constitute the artificial hip joint 1. However, the artificial joint is not limited to the artificial hip joint 1 according to the present disclosure, and may be, for example, an artificial knee joint, an artificial ankle joint, or an artificial shoulder joint.

The acetabular cup 10 has an acetabular fixing surface 14 with a substantially hemispherical shape, and a sliding surface 16 recessed in a substantially hemispherical manner. The femoral head ball 22 serving as a sliding member is disposed at one end of the femoral stem 20. Note that one aspect of the present disclosure includes the femoral head ball 22 to be fitted to one end of the femoral stem 20.

The femoral head ball 22 includes a sliding surface 23 created when the femoral head ball 22 slides against the acetabular cup 10. The sliding surface 23 can slide against the acetabular cup 10. The femoral head ball 22 functions as a hip joint by sliding against the sliding surface 16, which is recessed in a substantially hemispherical manner, of the acetabular cup 10. However, the sliding member in the present disclosure is not limited to the femoral head ball 22, and may be the acetabular cup 10. In this case, the acetabular cup 10 slides against the femoral head ball 22. A surface roughness Ra of the sliding surface 23 is not more than 0.01 μm. With this configuration, the coefficient of friction when the acetabular cup 10 and the femoral head ball 22 slide against each other can be reduced.

The acetabular fixing surface 14 is an external surface on a side closer to the acetabulum 94. The sliding surface 16 is also an inner surface or a contact surface in contact with the femoral head ball 22.

In an embodiment of the present disclosure, the acetabular cup 10 is made of polyethylene or ultra-high molecular weight polyethylene.

The femoral head ball 22 includes a composite ceramic containing alumina and at least one oxide other than alumina. This composition allows the femoral head ball 22 to be hard and have high strength. In the present embodiment, the femoral head ball 22 is made of a composite ceramic containing 65 to 96 wt % of alumina, and from 4 to 34.4 wt % of zirconia. With this composition, the femoral head ball 22 has higher strength and toughness compared to a ceramic made solely of alumina and not containing zirconia, and has higher hardness compared to a ceramic made of solely zirconia.

The femoral head ball 22 may contain at least 0.20 mass % of $SiO_2$, at least 0.22 mass % of $TiO_2$, and at least 0.12 mass % of MgO. With this composition, it is possible to mitigate a weakened sintering promotion effect caused by an increase in viscosity of the liquid phase formed at the sintering temperature. In the present embodiment, in the femoral head ball 22, the total content ratio of $SiO_2$, $TiO_2$, and MgO is from 0.6 to 4.5 mass %. With this composition, the effects of high densification and fine grain structure formation can be obtained.

In the present embodiment, the artificial joint is the artificial hip joint 1, and the sliding member is the femoral head ball 22 of the artificial hip joint 1. Therefore, wear resistance can be improved in the application of the femoral head ball 22 of the artificial hip joint 1. Note that wear resistance is evaluated by measuring weight loss resulting from wear of the acetabular cup 10 when the femoral head ball 22 and the acetabular cup 10 are repeatedly slid against each other.

Figure 2:
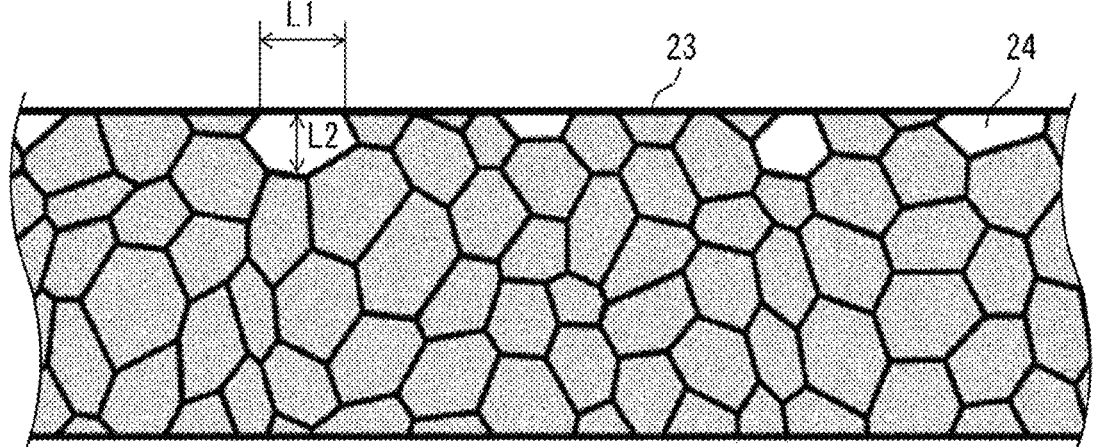
FIG. 2 is a schematic view illustrating a cross section of a sliding surface according to an embodiment of the present disclosure.

FIG. 2 is a schematic view of a cross section of the sliding surface 23 according to an embodiment of the present disclosure. The individual polygons illustrated in FIG. 2 denote individual crystal grains in a composite ceramic that is a polycrystalline body. In an embodiment of the present disclosure, the crystal grains are alumina crystal grains or zirconia crystal grains. However, no distinction is made in FIG. 2. Note that in FIG. 2, for convenience, the sliding surface 23 is illustrated as a flat surface. As illustrated in FIG. 2, the sliding surface 23 includes a plurality of recessed portions 24, each having an opening diameter L1 of not more than 2 µm. In the present embodiment, the opening diameter L1 represents the width of a small opening present in the sliding surface 23, and does not necessarily represent the diameter of a circle. The opening diameter L1 is determined by measuring the width of the opening in the sliding surface 23 captured by, for example, a scanning electron microscope (SEM). Additionally, binarization, circular conversion, or the like may be performed on the image of the sliding surface 23 by image processing software, and the opening diameter L1 may be calculated as the diameter when the image is converted to a circle having the same area. Because the sliding surface 23 includes the plurality of recessed portions 24, fluid present in the usage environment of the artificial hip joint 1 can be captured in the recessed portions 24. As a result, sliding with the acetabular cup 10 is smooth, and thus wear resistance can be improved.

At least some of the plurality of recessed portions 24 are formed by the lack of some crystal grains of the alumina contained in the composite ceramic. The recessed portions 24 can be formed in the sliding surface 23 by the lack of crystal grains of alumina containing an additive element other than aluminum and oxygen, for example. The shape of each recessed portion 24 is formed by the lack of some crystal grains of the alumina. Therefore, the recessed portion 24 may have an irregular shape and sharp edges. The shape of the recessed portion 24 may be a groove shape or a hole shape that becomes progressively narrower inward from the surface of the sliding surface 23, or may be a shape in which the width of the recessed portion increases until a predetermined depth from the opening.

The average crystal grain size of the alumina crystals is preferably not more than 2 µm. When the average crystal grain size of the alumina crystals is within this range, a larger number of recessed portions 24 each having an opening diameter L1 of not more than 2 µm, rather than not less than 2 µm, can be formed. The average crystal grain size can be determined by a linear intercept method using an enlarged image of a cross section of the composite ceramic captured by, for example, an SEM. In the present embodiment, the individual size of each crystal grain of alumina is from 0.05 to 3 µm. The individual diameter of each recessed portion formed by the lack of crystal grains of alumina is also not less than 0.05 µm.

A depth L2 to the bottom of the recessed portion 24 is not more than 2 µm. Here, the depth L2 to the bottom of the recessed portion 24 refers to the greatest distance of the distances from the opening of the recessed portion 24 to the bottom surface of the recessed portion 24 in the sliding surface 23. With this configuration, lubricating fluid is more likely to be retained between the friction surfaces, and wear of the friction material can be suppressed. The depth L2 can be measured by enlarged observation of a cross section perpendicular to the sliding surface 23 including the recessed portions 24, captured with an SEM or the like. Additionally, the sliding surface 23 including the recessed portions 24 may be viewed in an enlarged manner for measurement, by using a confocal laser microscope or the like having a high resolution for the shape measurement in the depth direction.

The sliding surface 23 includes at least 10,000 of the recessed portions 24 per square millimeter. With this configuration, a larger number of the recessed portions 24 in the sliding surface 23 can capture fluid present in the usage environment of the artificial hip joint 1, as compared to a sliding surface including a sliding surface with less than 10,000 of the recessed portions 24 per square millimeter. The upper limit of the number of recessed portions 24 per square millimeter is not particularly specified. However, an excessive number of recessed portions 24 affects the surface roughness Ra. When the surface roughness Ra increases, wear resistance decreases. Because of this, the number of recessed portions 24 per square millimeter is set to a range in which the surface roughness Ra does not exceed 0.01 µm.

Manufacturing Method

In an embodiment of the present disclosure, a method of manufacturing the femoral head ball 22 includes a polishing step and an acid treatment step. In the polishing step, the surface (sliding surface 23) of the composite ceramic containing alumina and at least one oxide other than alumina is polished. In the polishing step, the sliding surface 23 is polished so that the surface roughness Ra of the sliding surface 23 is not more than 0.01 µm. In the present embodiment, the at least one oxide other than alumina includes zirconia. With this composition, the femoral head ball 22 is stronger and has higher toughness compared to a zirconia-free composition. Additionally, the polishing step and the acid treatment step improve wear resistance.

In the acid treatment step, the surface of the femoral head ball 22 polished in the polishing step is treated with a strong acid solution to form the recessed portion 24 in the surface. In the present embodiment, in the acid treatment step, the surface of the femoral head ball 22 is brought into contact with a hydrochloric acid aqueous solution for from 5 minutes to 200 minutes by immersing the femoral head ball 22, which was polished in the polishing step, in the hydrochloric acid aqueous solution. In the acid treatment step, the recessed portion 24 is formed such that the depth L2 from the opening to the bottom of the recess 24 is not more than 2 µm. In addition, in the acid treatment step, at least 10,000 of the recessed portions 24 are formed in the sliding surface 2 per square millimeter. In the acid treatment step in the present embodiment, the method of manufacturing the femoral head ball 22 according to an embodiment of the present disclosure can be simplified and made cheaper because the femoral head ball 22 can be manufactured simply by immersing the femoral head ball 22 in a strong acid solution after the polishing step. Note that, herein, the acid treatment step may also be referred to as acid immersion or acid washing. In the acid treatment step, more preferably, the surface polished in the polishing step is brought into contact with the hydrochloric acid aqueous solution for from 30 minutes to 150 minutes.

The strong acid solution is a hydrochloric acid aqueous solution, a sulfuric acid aqueous solution, or a nitric acid aqueous solution, but is not limited to these aqueous solutions. The strong acid solution may also be a mixed solution of these aqueous solutions. In the present embodiment, the strong acid solution is a hydrochloric acid aqueous solution. With this configuration, the strong acid solution can be produced more easily than if the strong acid solution were a mixed solution of, for example, a sulfuric acid aqueous solution and a nitric acid aqueous solution.

In the method of manufacturing the femoral head ball 22 according to an aspect of the present disclosure, after the polishing step, the surface roughness Ra of the sliding surface 23 before the acid treatment step is not more than 0.01 μm, and the surface roughness Ra of the sliding surface 23 after the acid treatment step is also not more than 0.01 μm.

Note that, in an embodiment of the present disclosure, the method of manufacturing a sliding member may include a grinding step before the polishing step. In the grinding step, a composite ceramic containing alumina and at least one oxide other than alumina is ground to a predetermined shape (e.g., the shape of a femoral head ball). In the polishing step, the composite ceramic that has been ground into a predetermined shape in the grinding step may be polished.

EXAMPLES

Hereinafter, an aspect of the present disclosure will be described in more detail based on examples and comparative examples, but the aspects according to the present disclosure are not limited to these examples. In the present examples, femoral head balls of Example 1, Example 2, and Comparative Examples 1 to 3 described below were produced. Observation with SEM, roughness measurement, and a wear test were performed for the produced Examples and Comparative Examples.

A zirconia-toughened alumina (manufactured by KYOCERA Corporation) conforming to ISO 6474-2 was used as the material of the femoral head ball of Example 1. Specifically, a material containing 79.3 wt % of alumina, and 18.2 wt % of zirconia was used.

A zirconia-toughened alumina (manufactured by Kyocera Medical Corporation, Inc.) conforming to ISO 6474-2 was used as the material of the femoral head ball of Example 2. Specifically, a material containing 79 wt % of alumina, and 19 wt % of zirconia was used.

As the material of the femoral head ball of Comparative Example 1, a commercially-available zirconia-toughened alumina conforming to ISO 6474-2 and having the same size as those used as in Example 1 and Example 2 was used. The zirconia-toughened alumina contains about 75 wt % of alumina, and about 25 wt % of zirconia. A high-purity alumina was used as the material of the femoral head ball of Comparative Example 2. The high purity alumina contains at least 99.5 wt % of alumina. A Co—Cr—Mo alloy (ASTM F1537 compliant) was used as the material of the femoral head ball of Comparative Example 3.

Observation with SEM

The surface of each femoral head ball 22 was platinum-deposited and the surface of the femoral head ball 22 was observed with a scanning electron microscope (SEM). A secondary electron image was obtained at a magnification of from 1000× to 30000×.

Figure 3:
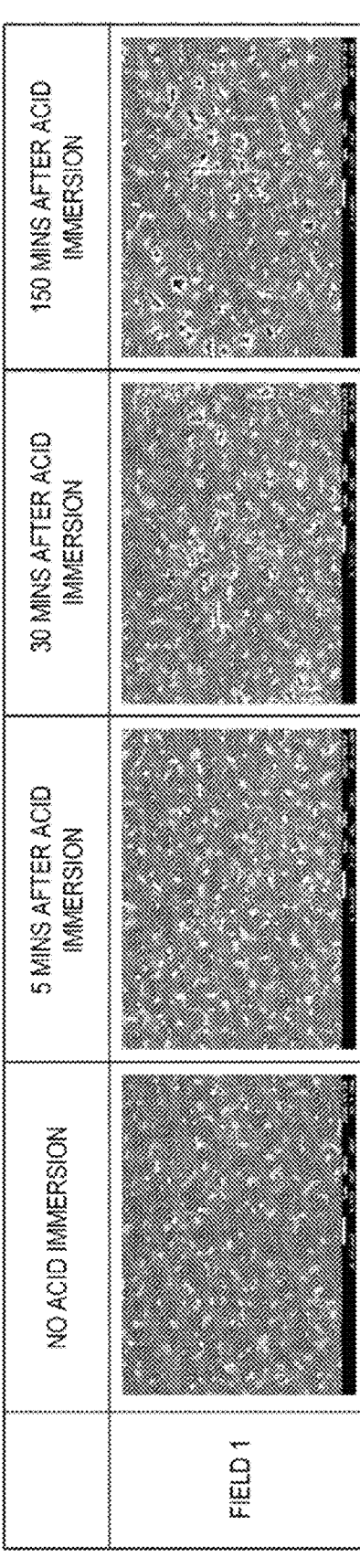
FIG. 3 is a diagram showing the state of occurrence of recessed portions according to acid immersion time of the femoral head ball according to an example of the present disclosure.

FIG. 3 is a diagram showing states of occurrence of the recessed portions when the time for which the femoral head ball of Example 1 is to be immersed in the hydrochloric acid aqueous solution is changed. As shown in FIG. 3, the sliding surface 23 of the femoral head ball after 5 minutes of acid immersion was rough compared to that before the acid immersion, indicating that the recessed portions 24 were formed. In the sliding surface 23 of the femoral head ball 22 after 30 minutes of acid immersion, a larger number of recessed portions were formed compared to the sliding surface 23 of the femoral head ball 22 after 5 minutes of acid immersion. In the sliding surface 23 of the femoral head ball after 150 minutes of acid immersion, a larger number of recessed portions were formed compared to the sliding surface 23 of the femoral head ball 22 after 30 minutes of acid immersion. As a result, FIG. 3 shows that the recessed portions 24 can be formed in the surface of the sliding surface 23 by bringing the surface of the composite ceramic into contact with the hydrochloric acid aqueous solution for no less than 5 minutes.

Figure 4:
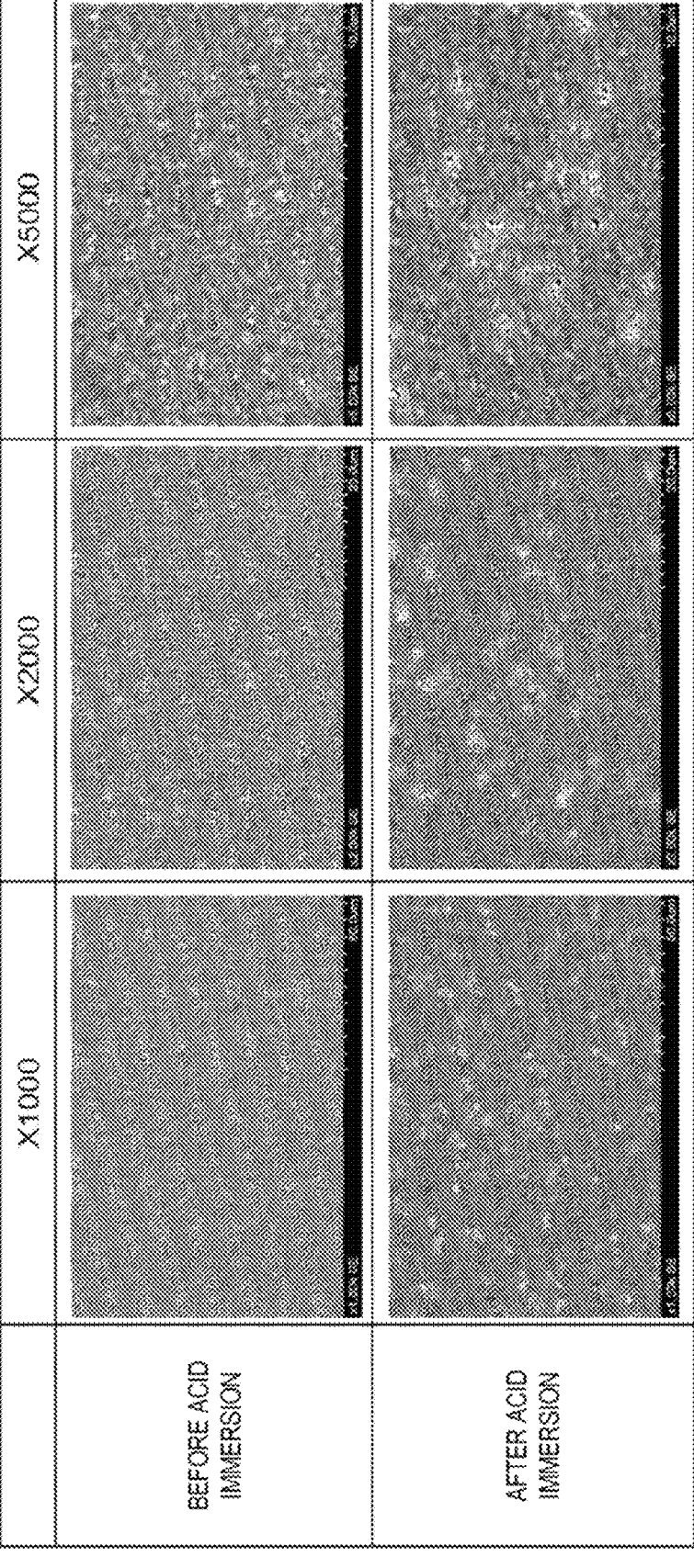
FIG. 4 is enlarged views of the recessed portions in the sliding surface of the femoral head ball before and after acid immersion (before and after acid washing) according to an example of the present disclosure.
Figure 5:
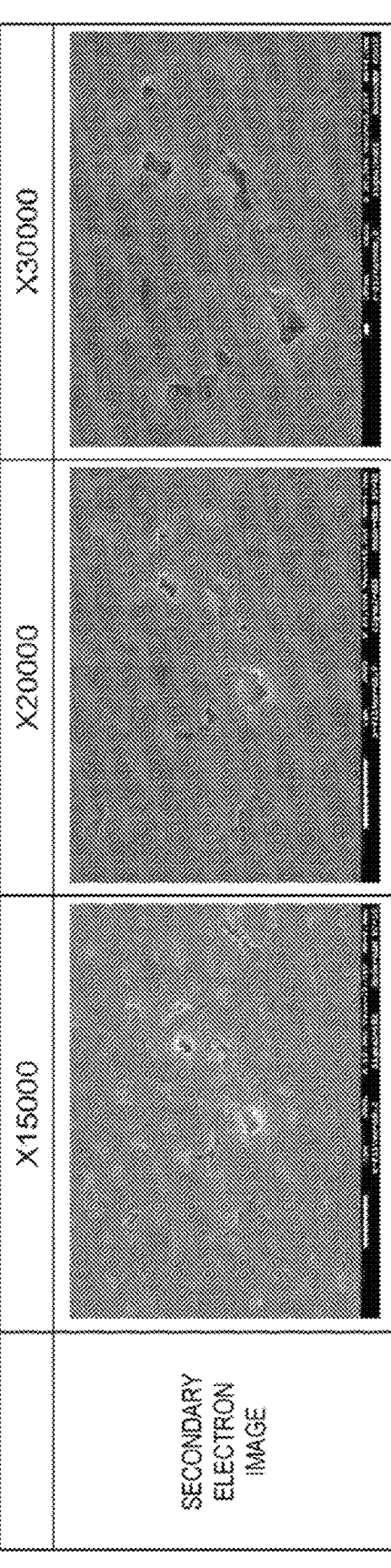
FIG. 5 is enlarged views of the recessed portions in the sliding surface after acid immersion (after acid washing) of the femoral head ball according to an example of the present disclosure.

FIG. 4 is enlarged views of the recessed portions in the sliding surface of the femoral head ball of Example 1 before and after acid immersion (before and after acid washing). FIG. 5 is enlarged views of the recessed portions of the sliding surface of the femoral head ball of Example 1 after being immersed in acid (after being washed with acid). As shown in FIG. 4 and FIG. 5, when viewed at a magnification of 5000×, fine protrusions and recesses were formed in the surface of the sliding surface before the acid immersion. This corresponds to the surface roughness of the sliding surface of the femoral head ball prior to acid immersion. FIG. 4 shows the result that, when viewed at a magnification of 1000×, the recessed portions were formed in the sliding surface after the acid immersion. FIG. 4 also shows the result that, when viewed at a magnification of 5000×, black spots were present on the sliding surface after the acid immersion. These black spots were formed by the lack of some of the crystals of alumina contained in the composite ceramic.

Laser Microscope Observation

Figure 6:
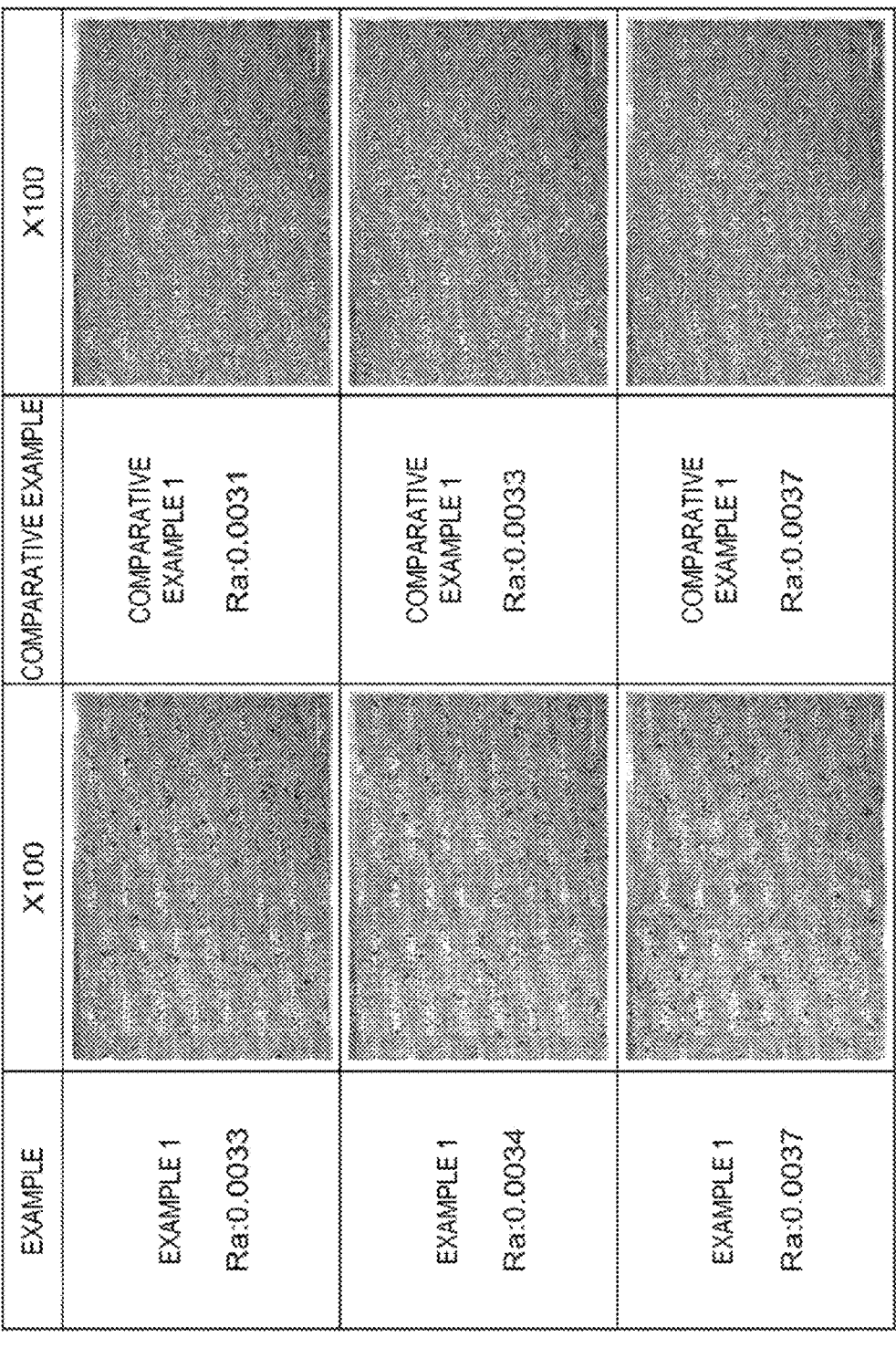
FIG. 6 is a diagram comparing the surface roughness of femoral head balls after acid immersion according to an example of the present disclosure.

The surface of each femoral head ball was observed at 100× magnification with a confocal laser microscope (manufactured by Olympus Corporation). FIG. 6 is a diagram comparing the surface roughness of the sliding surfaces of the femoral head ball of Example 1 after acid immersion and Comparative Example 1 when no acid immersion is performed. Note that the lower-right scale in each photograph corresponds to 15 μM. As shown in FIG. 6, a large number of recessed portions were formed in the surface of Example 1, compared to the surface of Comparative Example 1.

Roughness Measurement

In accordance with JIS B0601, the roughness curve of the femoral head ball at an apex portion was obtained with a reference length of 0.08 mm and a number of intervals of 5, by using a contact-type roughness measuring instrument (SV-3100SA, manufactured by Mitutoyo Corporation). Cut off with a Gaussian filter of λc: 0.08 mm and λs: 0.0008 mm was performed, and the arithmetic mean roughness Ra was measured.

TABLE 1

| n | Example 1 | Example 2 | Comparative Example 1 |
|---|---|---|---|
| 1 | 0.0027 | 0.0058 | 0.0030 |
| 2 | 0.0038 | 0.0033 | 0.0037 |
| 3 | 0.0036 | 0.0022 | 0.0026 |
| 4 | 0.0033 | 0.0029 | 0.0031 |
| 5 | 0.0034 | 0.0029 | 0.0033 |
| 6 | 0.0037 | 0.0026 | 0.0037 |
| Average | 0.0034 | 0.0033 | 0.0032 |

Table 1 is a table showing the surface roughness of the femoral head ball of Examples 1 and 2 after acid immersion, and the surface roughness of the femoral head ball of Comparative Example 1 when no acid immersion is performed. n in Table 1 is the sample number of each Example and Comparative Example. As shown in Table 1, the average surface roughness of the femoral head ball 22 after acid immersion was 0.0034 for Example 1, 0.0033 for Example 2, and 0.0032 for Comparative Example 1. That is, the average surface roughness of the femoral head ball 22 after acid immersion was substantially equal across Example 1, Example 2, and Comparative Example 1. This result indicates that, in the present embodiment, the recessed portions formed in the femoral head ball have little effect on the surface roughness of the femoral head ball. It can also be seen that, the surface roughness Ra of the surface is at the same level even for the femoral head balls of Comparative Example 2 and Comparative Example 3, and no surface roughness Ra was more than 0.01 nm.

Wear Test

A femoral head ball with an outer diameter of 40 mm was produced using a zirconia-toughened alumina material, and a wear simulation test conforming to ISO 14242-1 and ISO 14242-2 was performed. A crosslinked ultra-high molecular weight polyethylene liner (cup), which underwent gas plasma sterilization, was used as the object against which the femoral ball head 22 was slid. The test was performed with the number of samples n=3 for each Example and Comparative Example. The amount of wear was determined by measuring the change in weight of the liner every 500,000 cycles, and measuring the difference between the weight loss from the start of the test and the load soak. The amount of wear was measured every 500,000 cycles up to five million cycles, and the average value of the amounts of wear for n=3 was calculated for each cycle.

Figure 7:
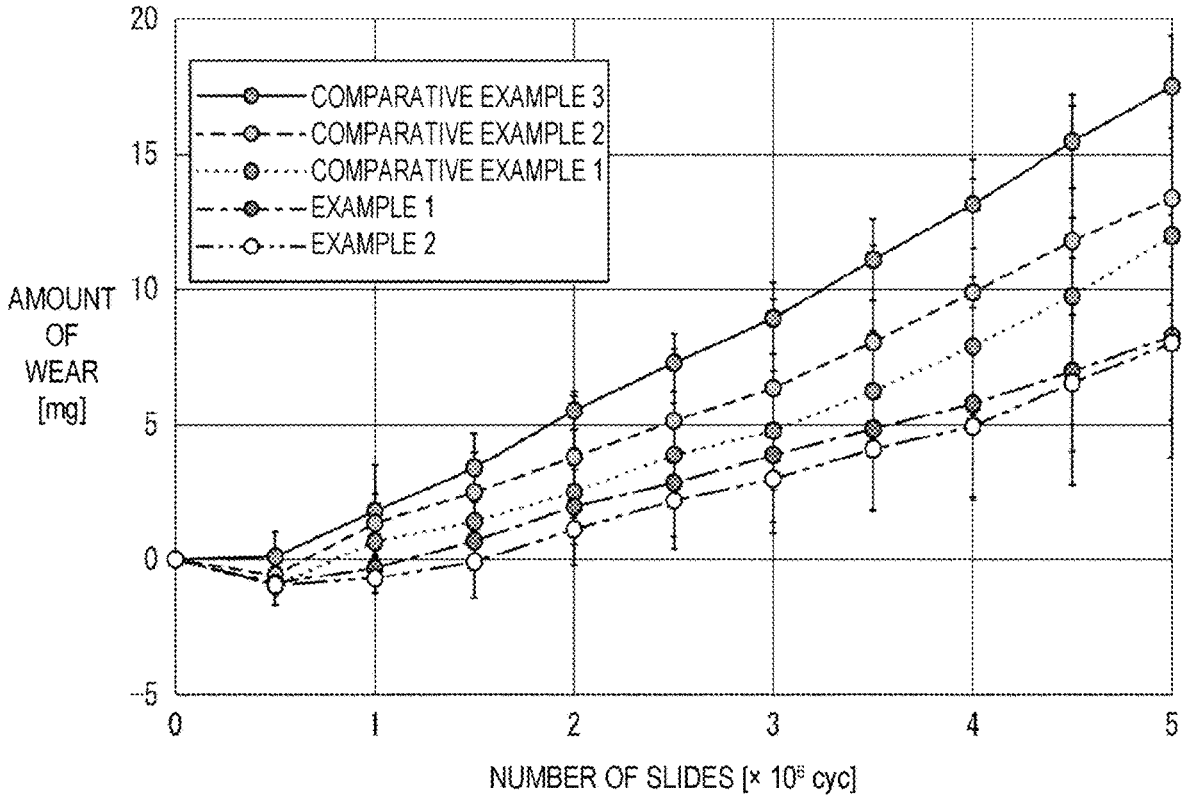
FIG. 7 is a graph showing results of a wear test performed on femoral head balls after acid immersion.

FIG. 7 shows the results of the wear test performed on the femoral head balls after acid immersion. The vertical axis in FIG. 7 represents the amount of wear of the liner slid against the femoral head ball in mg. The horizontal axis in FIG. 7 represents the number of slides. For example, a value of five along the horizontal axis in FIG. 7 means five million cycles.

As shown in FIG. 7, the amounts of wear of Example 1 and Example 2 after five million cycles were each approximately 8 mg. In contrast, the amounts of wear of Comparative Example 1, Comparative Example 2, and Comparative Example 3 after five million cycles were approximately 12 mg, approximately 13.5 mg, and approximately 17.5 mg, respectively. The amounts of wear of Example 1 and Example 2, in which the recessed portions were formed, were each lower than the amounts of wear of Comparative Example 1, Comparative Example 2, and Comparative Example 3. Therefore, it can be seen that forming the plurality of recessed portions improves wear resistance.

The invention according to the present disclosure has been described above based on the drawings and examples. However, the invention according to the present disclosure is not limited to each embodiment described above. That is, the invention according to the present disclosure can be variously modified within the scope indicated in the present disclosure, and an embodiment to be obtained by appropriately combining technical means disclosed in different embodiments is also included in the technical scope of the invention according to the present disclosure. In other words, note that a person skilled in the art can easily make various variations or modifications based on the present disclosure. Note that these variations or modifications are included within the scope of the present disclosure.

REFERENCE SIGNS

1 Artificial hip joint (artificial joint)
10 Acetabular cup (sliding member)
16, 23 Sliding surface
22 Femoral head ball (sliding member)
24 Recessed portion
L1 Opening diameter
L2 Depth to bottom of recessed portion

The invention claimed is:

1. A method for manufacturing a sliding member, the method comprising:
immersing a surface of a base material in a one or more strong acid solution or acid washing the surface of the base material, the base material comprising a composite ceramic, the composite ceramic including an alumina and at least one oxide except alumina, wherein the composite ceramic comprises from 65 to 96 wt % of alumina and from 4 to 34.4 wt % of zirconia, wherein the sliding member is an artificial bone head, and the surface of the base material is configured to be in contact with a member when the artificial bone head and the member are used in a human body, the member being an acetabular cup or a liner.

2. The method according to claim 1, further comprising sanding the surface of the base material before the immersing or the acid washing.

3. The method according to claim 2, wherein, after the sanding, a surface roughness Ra of the surface before the immersing or the acid washing is not more than 0.01 μm, and the surface roughness Ra of the surface after the acid washing is also not more than 0.01 μm.

4. The method according to claim 1, wherein a recessed portion is formed by the immersing or the acid washing, and the recessed portion is not more than 2 μm in depth from an opening to a bottom.

5. The method according to claim 1, wherein, by the immersing or the acid washing, at least 10,000 recessed portions are formed in a sliding surface per square millimeter, the sliding surface being configured to slide against a constituent member constituting an artificial joint.

6. The method according to claim 1, wherein the one or more strong acid solution is one or more selected from the group consisting of a hydrochloric acid aqueous solution, a sulfuric acid aqueous solution, and a nitric acid aqueous solution.

7. The method according to claim 6, wherein, in the immersing or acid washing, the surface is brought into contact with the hydrochloric acid aqueous solution for no less than 5 minutes.

8. The method according to claim 6, wherein, in the immersing or acid washing, the surface is brought into contact with the hydrochloric acid aqueous solution for no less than 30 minutes.

9. The method according to claim 6, wherein, in the immersing or acid washing, the surface is brought into contact with the hydrochloric acid aqueous solution for no less than 150 minutes.

* * * * *